US010702662B2

(12) United States Patent
Wei (10) Patent No.: US 10,702,662 B2
(45) Date of Patent: Jul. 7, 2020

(54) SYRINGE NEEDLE SHIELD AND BASE FOR THE SAME

(71) Applicant: Ching-Hsiang Wei, Taichung (TW)

(72) Inventor: Ching-Hsiang Wei, Taichung (TW)

( * ) Notice: Subject to any disclaimer, the term of this patent is extended or adjusted under 35 U.S.C. 154(b) by 117 days.

(21) Appl. No.: 15/990,641

(22) Filed: May 27, 2018

(65) Prior Publication Data

US 2018/0353707 A1 Dec. 13, 2018

(30) Foreign Application Priority Data

Jun. 7, 2017 (TW) .............................. 106118932 A (51) Int. Cl.
*A61M 5/32* (2006.01)
*A61M 5/50* (2006.01)
*A61M 5/34* (2006.01)

(52) U.S. Cl.
CPC .......... *A61M 5/3216* (2013.01); *A61M 5/321* (2013.01); *A61M 5/32* (2013.01); *A61M 5/3202* (2013.01); *A61M 5/34* (2013.01); *A61M 5/50* (2013.01); *A61M 2005/3217* (2013.01); *A61M 2205/276* (2013.01)

(58) Field of Classification Search
CPC ........ A61M 5/002; A61M 2005/14256; A61M 5/3216; A61M 2005/1426; A61M 2005/3223; A61M 5/50; A61M 2005/3217; A61M 5/32; A61M 5/31; A61M 5/178; A61M 5/3205; A61M 5/321; A61M 5/3219; A61M 5/31571; A61M 5/322; A61M 5/3202; A61M 5/158; A61M 5/3213; A61M 2005/3254; A61M 25/0612; A61M 25/0618
See application file for complete search history.

(56) References Cited

U.S. PATENT DOCUMENTS

| 5,017,189 A * | 5/1991 | Boumendil ......... A61M 5/3216 604/192 |
| 5,603,699 A * | 2/1997 | Shine ................... A61M 5/3216 604/110 |
| 5,925,032 A * | 7/1999 | Clements ................ A61M 5/34 604/192 |
| 6,120,482 A * | 9/2000 | Szabo ................. A61M 5/3216 128/919 |
| 8,622,960 B2 * | 1/2014 | Madin ................. A61M 5/3216 604/110 |
| 9,494,264 B2 * | 11/2016 | Avery ................... A61J 1/1418 |

(Continued)

*Primary Examiner* — Nathan R Price
*Assistant Examiner* — Jacob Michael Lindsay
(74) *Attorney, Agent, or Firm* — Pai Patent & Trademark Law Firm; Chao-Chang David Pai (57) ABSTRACT

A syringe needle shield that includes a first part and a second part. The first part is connected to the second part by a pivotable first connection portion. The second part is pivotable on the first connection portion toward the first part, and a needle hub is clamped between the first and second parts. The first and second parts are securely connected to each other by the first snapping portion which cannot be unlocked from each other. The first part is connected to a needle shield by a flexible plate. The shield receives a push force from its back so as to move from a first position to a second position. When the shield is located at the second position, a restriction portion is fixedly engaged with an engaging portion.

7 Claims, 13 Drawing Sheets

(56) References Cited

U.S. PATENT DOCUMENTS

| | | | | |
|---|---|---|---|---|
| 2002/0193744 | A1* | 12/2002 | Alesi | A61M 5/3216 |
| | | | | 604/192 |
| 2013/0331793 | A1* | 12/2013 | Gonzales | A61M 5/3219 |
| | | | | 604/192 |
| 2014/0052072 | A1* | 2/2014 | Simas, Jr. | A61M 5/3202 |
| | | | | 604/192 |
| 2014/0221872 | A1* | 8/2014 | Lin | A61M 5/3216 |
| | | | | 600/576 |
| 2014/0364804 | A1* | 12/2014 | Stillson | A61M 5/5086 |
| | | | | 604/111 |
| 2015/0165133 | A1* | 6/2015 | Zhang | A61M 5/3202 |
| | | | | 604/192 |
| 2015/0273159 | A1* | 10/2015 | Zhang | A61M 5/3216 |
| | | | | 604/263 |
| 2016/0074598 | A1* | 3/2016 | Wang | A61M 5/3216 |
| | | | | 604/192 |
| 2016/0158458 | A1* | 6/2016 | Feng | A61M 5/3216 |
| | | | | 604/110 |
| 2016/0220766 | A1* | 8/2016 | Kawano | A61M 5/3213 |
| 2016/0296712 | A1* | 10/2016 | Minix | A61M 5/3216 |
| 2016/0317755 | A1* | 11/2016 | Wang | A61M 5/3216 |
| 2017/0014579 | A1* | 1/2017 | Derby | A61M 5/343 |

* cited by examiner

SYRINGE NEEDLE SHIELD AND BASE FOR THE SAME

BACKGROUND OF THE INVENTION

1. Field of the Invention

The present invention relates to a syringe needle shield, and, more particularly, to a syringe needle shield that shields a used syringe needle to protect people from being hurt by the used syringe needle.

2. Descriptions of Related Art

The conventional syringe generally includes a cover which is mounted to the syringe needle hub so as to protect medical staff from being hurt or contaminated by the used needles. The patient's blood or body liquid is attached to the used needle, so the used needle has to be isolated to prevent people from coming in contact with the needles and to keep the risk of infection away from people. Therefore, the used needles have to be properly shielded.

The present invention is intended to provide a used needle shield to achieve the purposes mentioned above.

SUMMARY OF THE INVENTION

The objective of the present invention is to provide a needle shield for shielding the used needle so as to prevent people from being injured by the used needle.

The present invention relates to a syringe needle shield and comprises a first part and a second part. The first side of the first part is connected to the first side of the second part by a pivotable first connection portion. The second part is pivotally movable toward the first part on the first connection portion.

A first snapping portion includes a recess located inside of the first part and a hook located inside of the second part. When the second part is pivotally moved to the first part, the hook is fixedly connected with the recess and cannot be separated from the recess.

A first room and a second room are respectively defined in the first part and the second part. When the first part is connected to the second part by the first snapping portion, the first room and the second room together define a chamber. The chamber is vertically defined through the top and the bottom of each of the first part and the second part.

A first groove and a second groove are respectively defined inside of the first part and the inside of the second part, and in communication with the first room and the second room. When the first part is connected to the second part by the first snapping portion, the first groove and the second groove together define an annular groove inside of the chamber.

A positioning device has a first positioning portion and a second positioning portion. The first positioning portion and the second positioning portion are respectively located at the second part and at a shield. The first positioning portion and the second positioning portion respectively include a restriction portion and an engaging portion. A flexible plate is connected between the underside of the shield and the first part, so that the shield is movable between a first position to a second position. When the shield is located at the second position, the restriction portion is engaged with the engaging portion.

Preferably, the syringe needle shield further comprises a third part. The second side of the first part is connected to the first side of the third part by a pivotable second connection portion. The second snapping portion includes an assistance hook located at inside of the third part, and an assistance recess that is located outside of the second part. When the first part is connected to the second part by the first snapping portion, the third part is pivotable toward the first part and the second part on the second connection portion, and the assistance hook is engaged with the assistance recess.

Preferably, the restriction portion extends from each of the two sides of the first positioning portion. The restriction portion has an inclined face. Each of two sides of the shield includes the engaging portion. When the shield is moved from the first position to the second position, the engaging portion is guided along the inclined face and engages with the restriction portion.

Preferably, the two sides of the shield respectively extend toward the first positioning portion. Each of the two sides of the shield includes a notch located corresponding to the restriction portion on the same side. The engaging portion is located at the lower portion of the notch which accommodates the restriction portion and the inclined face.

Preferably, the two sides of the first positioning portion respectively extend toward the shield. The two sides of the shield respectively extend toward the first positioning portion. The restriction portion and the inclined face are located at an extension portion of the first positioning portion. The engaging portion is located at an extension portion of the shield.

Preferably, the two sides of the first positioning portion respectively extend toward the shield. The restriction portion and the inclined face are located at the extension portion of the first positioning portion.

Preferably, the first positioning portion is located on the second part, and the second positioning portion is located on the shield.

In another embodiment, the first positioning portion is located on the shield, and the second positioning portion is located on the second part.

The present invention also provides a base of a syringe needle shield. The base comprises a first part and a second part. The first side of the first part is connected to the first side of the second part by a pivotable first connection portion. The second part is pivotally movable toward the first part on the first connection portion. A flexible plate is connected between the underside of the shield and the first part.

A first snapping portion includes a recess inside of the first part and a hook inside of the second part, and the hook is fixedly connected with the recess and cannot be separated from the recess.

A first room and a second room are respectively defined in the first part and the second part. When the first part is connected to the second part by the first snapping portion, the first room and the second room together define a chamber. The chamber is vertically defined through the top and the bottom of each of the first part and the second part.

A first groove and a second groove are respectively defined on the inside of the first part and the inside of the second part, and in communication with the first room and the second room. When the first part is connected to the second part by the first snapping portion, the first groove and the second groove together define an annular groove inside of the chamber.

Preferably, the base of a syringe needle shield further comprises a third part. The second side of the first part is connected to the first side of the third part by a pivotable second connection portion. The second snapping portion includes an assistance hook located inside of the third part, and an assistance recess located outside of the second part. When the first part is connected to the second part by the first snapping portion, the third part is pivotable toward the first part and the second part on the second connection portion. The assistance hook is engaged with the assistance recess.

The advantages of the present invention are that by fixing the first and second parts to the needle bub of the syringe, the syringe needle shield of present invention is easily installed on the needle hub and may not be separated from the needle hub.

The base of the present invention can be used cooperatively with known syringes, such as the straight needle hub, the indwelling needle hub, the connector between winged infusion set and infusion tube, and the insulin syringe. The needle hub of the above mentioned syringes needs no additional amendment.

The third part is connected to the first and second parts, so that the connection between the base of the syringe needle shield of the present invention and the needle hub is stable and secured.

The shield is pivotable to change its position according to practical needs. The shield at the first position does not impede the medical person's injection action. The shield can be pushed from the first position to the second position to shield the used needle to ensure safety to people.

By the connection between the restriction portion and the engaging portion, the shield at the second position is fixed to the base and cannot be moved back to the first position. The used needle would never be exposed in any situation.

The combination of the first and second parts is able to rotate about the needle hub, and is convenient for the medical professional to adjust and does not affect the position for properly using the syringe.

The syringe needle shield of the present invention is manufactured separately from the syringe, and the production line is not combined with the production line of syringes to avoid the need and cost of changing the production line of the syringes.

The shape and structure of the needle shield is easily manufactured and is suitable for mass production.

The volume and weight of the syringe needle shield of the present invention does not affect the user's ability to hold and operate the syringe.

The present invention will become more obvious from the following description when taken in conjunction with the accompanying drawings which show, for purposes of illustration only, preferred embodiments in accordance with the present invention.

DETAILED DESCRIPTION OF THE PREFERRED EMBODIMENT

In order to interpret the main spirit and features of the present invention, multiple embodiments of the present invention are disclosed. The parts disclosed are disclosed according to the sizes, specifications, deformations or displacements that are proper for interpretation, and may not be identical as real parts.

Referring to FIGS. 1-5, the syringe needle shield of the present invention comprises a first part 10 and a second part 20. The first side of the first part 10 is connected to the first side of the second part 20 by a pivotable first connection portion 41, so that the second part 20 is pivotally movable toward the first part 10 on the first connection portion 41. A first snapping portion 43 is located at the inside of the first part 10 and the second part 20. The first snapping portion 43 includes a recess 431 at the inside of the first part 10 and a hook 432 at the inside of the second part 20 which is fixedly connected with the recess 431 and cannot be separated from the recess 431. A first room 11 and a second room 21 are respectively defined in the first part 10 and the second part 20. A first groove 13 and a second groove 23 are respectively defined in the inside of the first part 10 and the inside of the second part 20, and in communication with the first room 11 and the second room 21. When the first part 10 is connected to the second part 20 by the first snapping portion 43, the first groove 13 and the second groove 23 together define an annular groove 14 in the inside of the chamber 12. The chamber 12 is vertically defined through the top and the bottom of each of the first part 10 and the second part 20. A positioning device 50 has a first positioning portion 51 and a second positioning portion 52. The first positioning portion 51 is located at the second part 20, and the second positioning portion 52 is connected to a shield 60. The first positioning portion 51 and the second positioning portion 52 respectively include a restriction portion 53 and an engaging portion 55, and the restriction portion 53 cannot be separated from the engaging portion 55 once they are engaged with each other. A flexible plate 61 is connected between the underside of the shield 60 and the first part 10, so that the shield 60 is pivotally movable from a first position P1 to a second position P2 on the flexible plate 61. When the shield 60 is located at the second position P2, the restriction portion 53 is engaged with the engaging portion 55.

Figure 5:
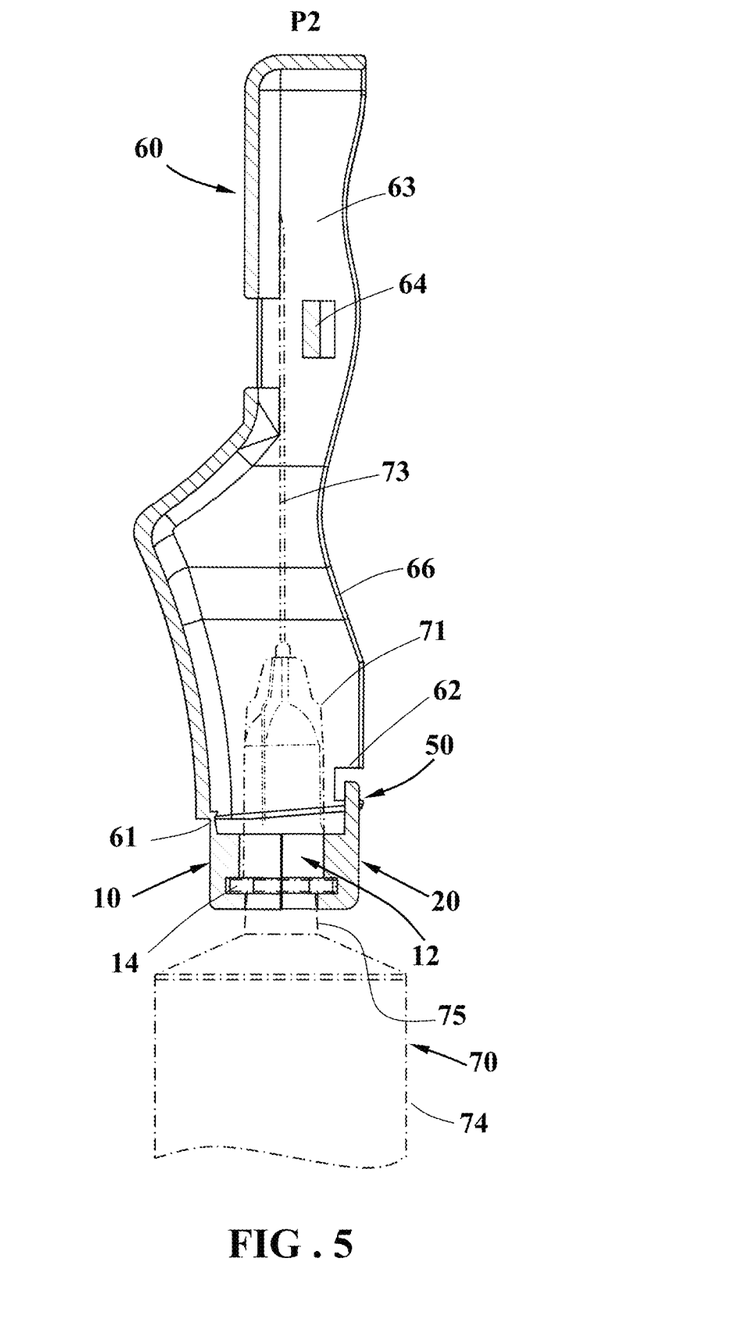
FIG. 5 is a cross sectional view to show the syringe needle shield of the present invention and the syringe needle that is shielded by the syringe needle shield of the present invention.
Figure 6:
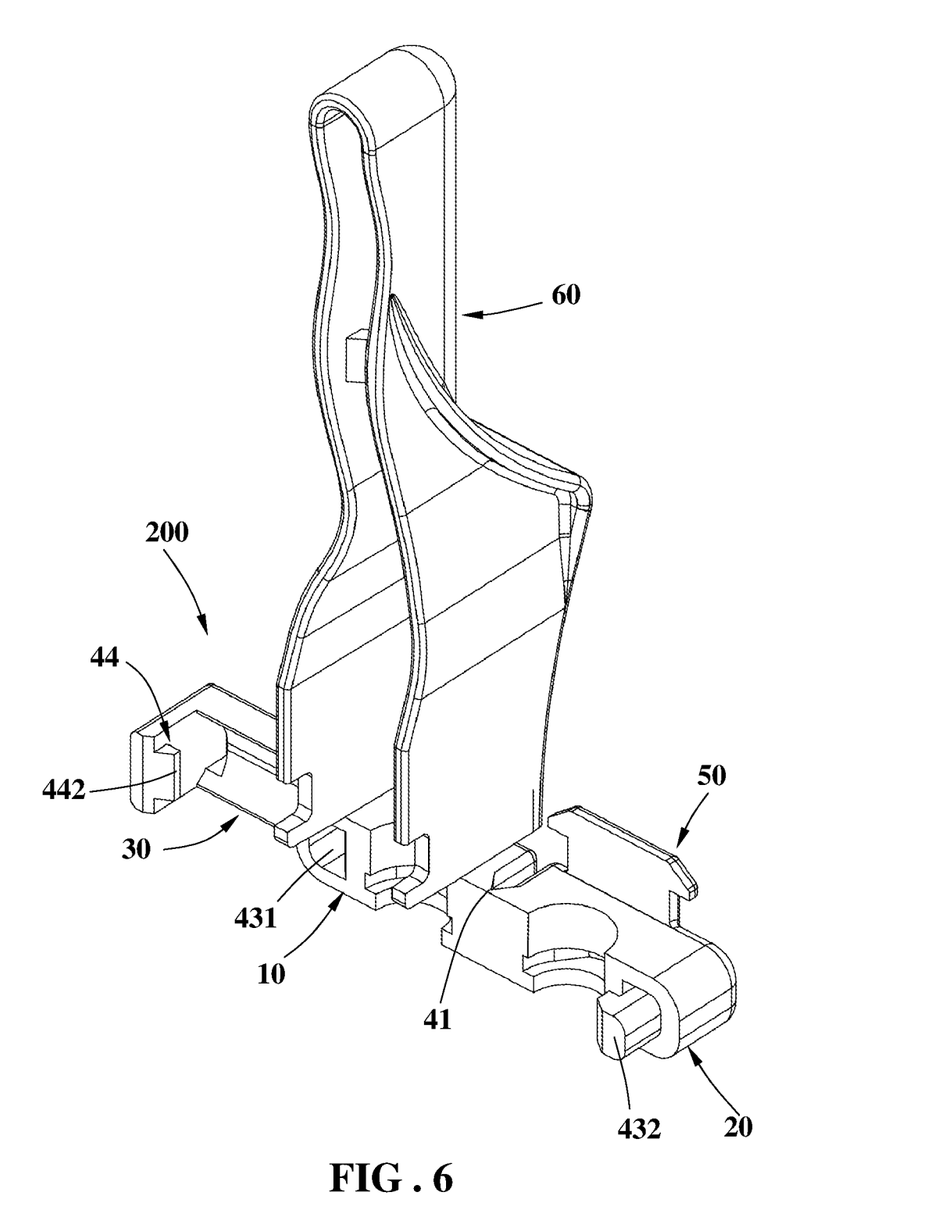
FIG. 6 is a perspective view to show the second embodiment of the open status of the base of the needle shield of the present invention.
Figure 7:
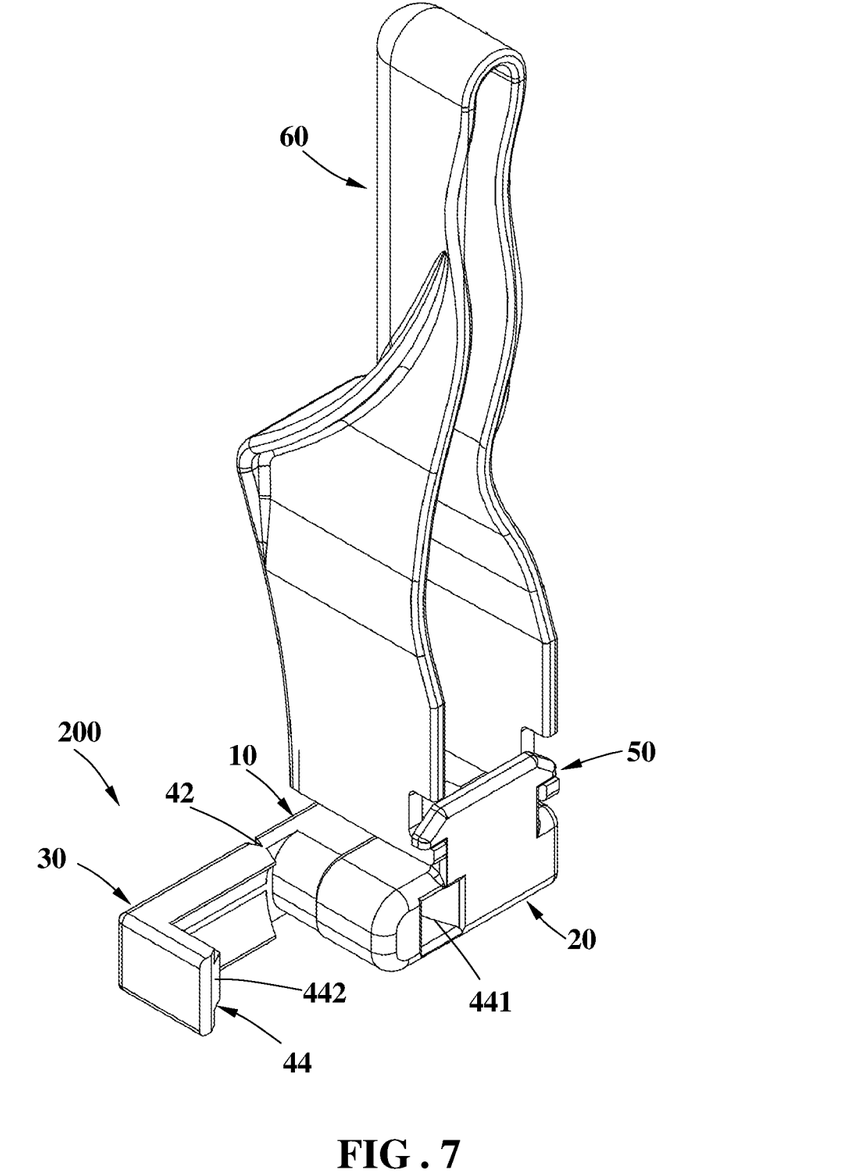
FIG. 7 is a perspective view to show the second embodiment of the needle shield of the present invention.
Figure 8:
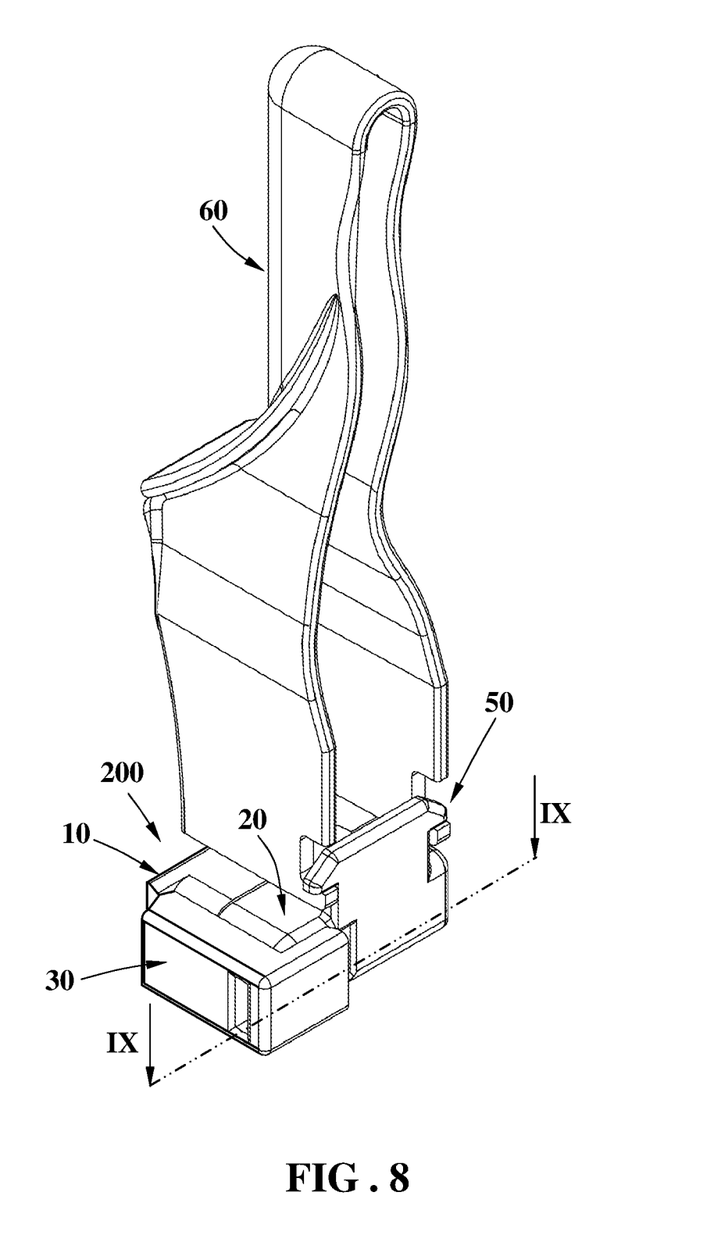
FIG. 8 is another perspective view of the second embodiment of the needle shield of the present invention.
Figure 9:
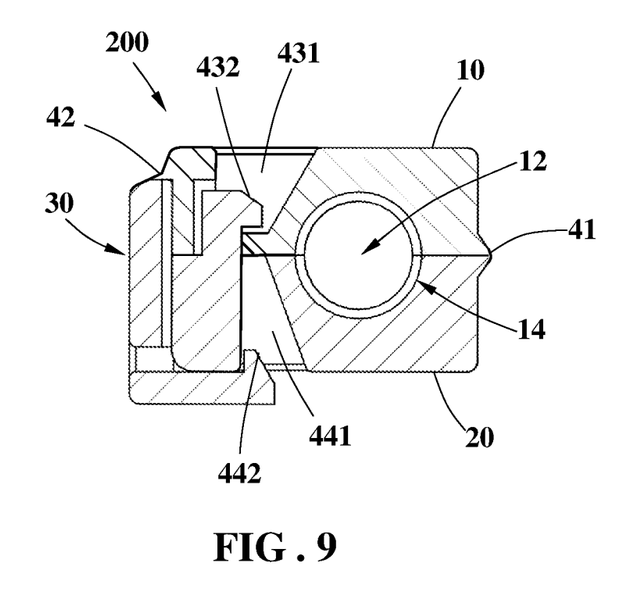
FIG. 9 is a cross sectional view, taken along plane IX-IX of FIG. 8.

FIG. 5 shows the shield 60 with a syringe 70 placed inside. The syringe 70 is well known in the art. The syringe 70 includes a needle hub 71, a needle 73 and a barrel 74 which includes a barrel tip 75 on which the needle hub 71 is mounted. The needle hub 71 is located between the first room 11 of the first part 10 and the second room 21 of the second part 20. The flange 72 of the needle hub 71 is located in the first and second grooves 13, 23. By pivotally moving the second part 20 toward the first part 10 on the first connection portion 41, the needle hub 71 is located in the chamber 12 defined by the first room 11 and the second room 21. The flange 72 of the needle hub 71 is located in the annular groove 14 defined by the first groove 13 and the second groove 23. The shield 60 includes a space 63 for accommodating the needle 73. An inclined stop 64 extends from one of the two sidewalls 66 of the space 63 that tilts relative to the space 63.

Figure 1:
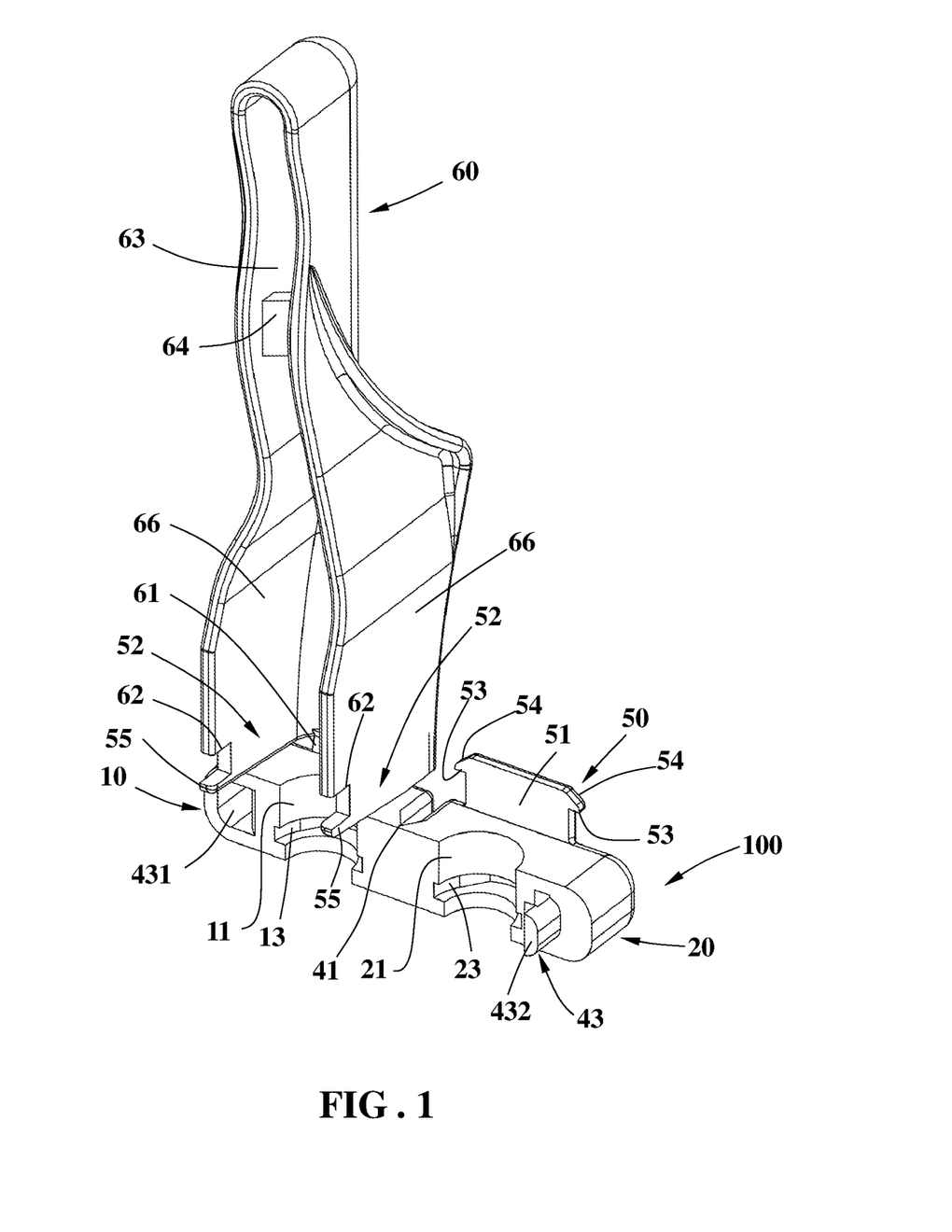
FIG. 1 is a perspective view to show the open status of the base of the needle shield of the present invention.
Figure 2:
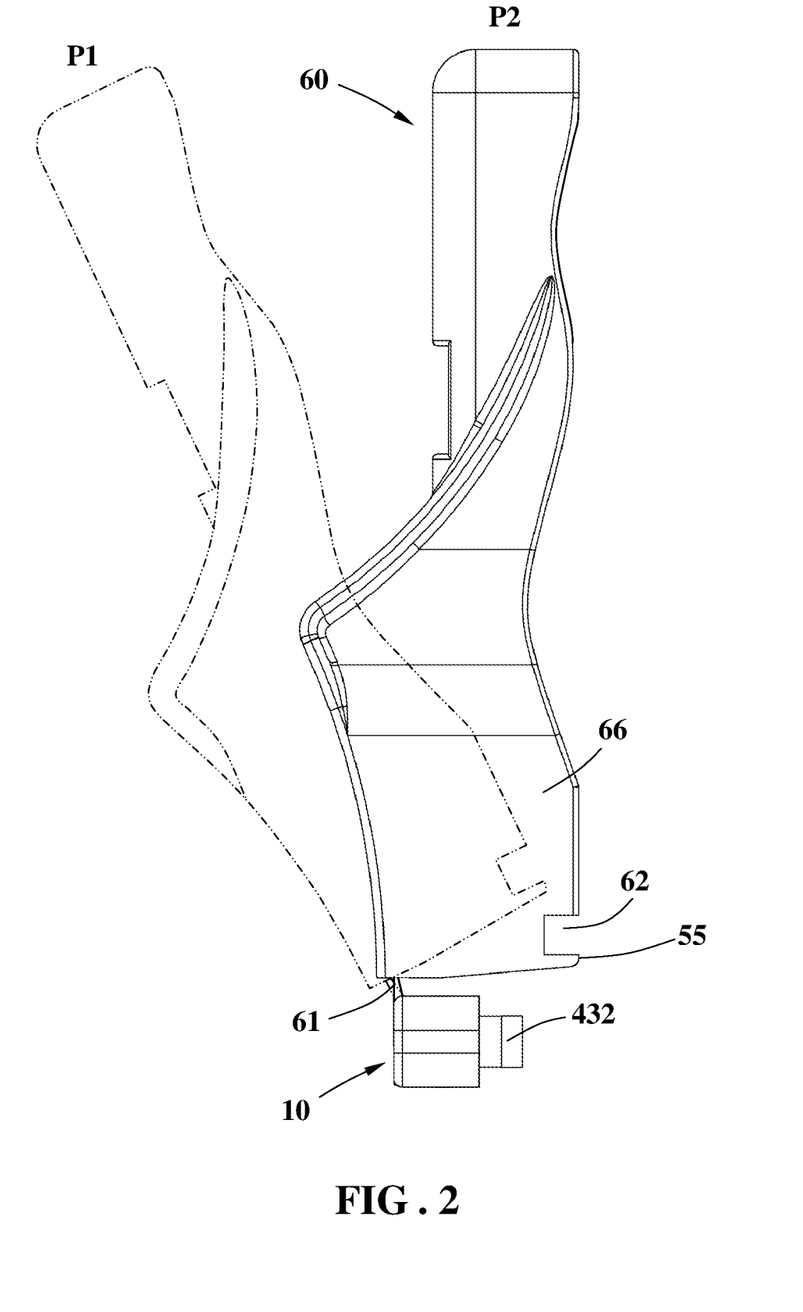
FIG. 2 is a left side view of the needle shield base of FIG. 1 and also shows that the shield is located at the first and second positions.

As shown in FIGS. 1 and 2, the shield 60 receives force from its back via the flexible plate 61 so that the shield 60 moves from the first position P1 to the second position P2. The shield 60 located at the first position P1 does not impede the medical professional to proceed with an injection action. After the injection action is completed, the medical professional pushes the back of the shield 60 with one hand to move the shield 60 from the first position P1 to the second position P2. The needle 73 is guided by the stop 64 and enters into the space 63. The needle hub 71 and the needle 73 are shielded by the shield 60, and the needle 73 cannot pass the stop 64 from the opposite direction.

Figure 3:
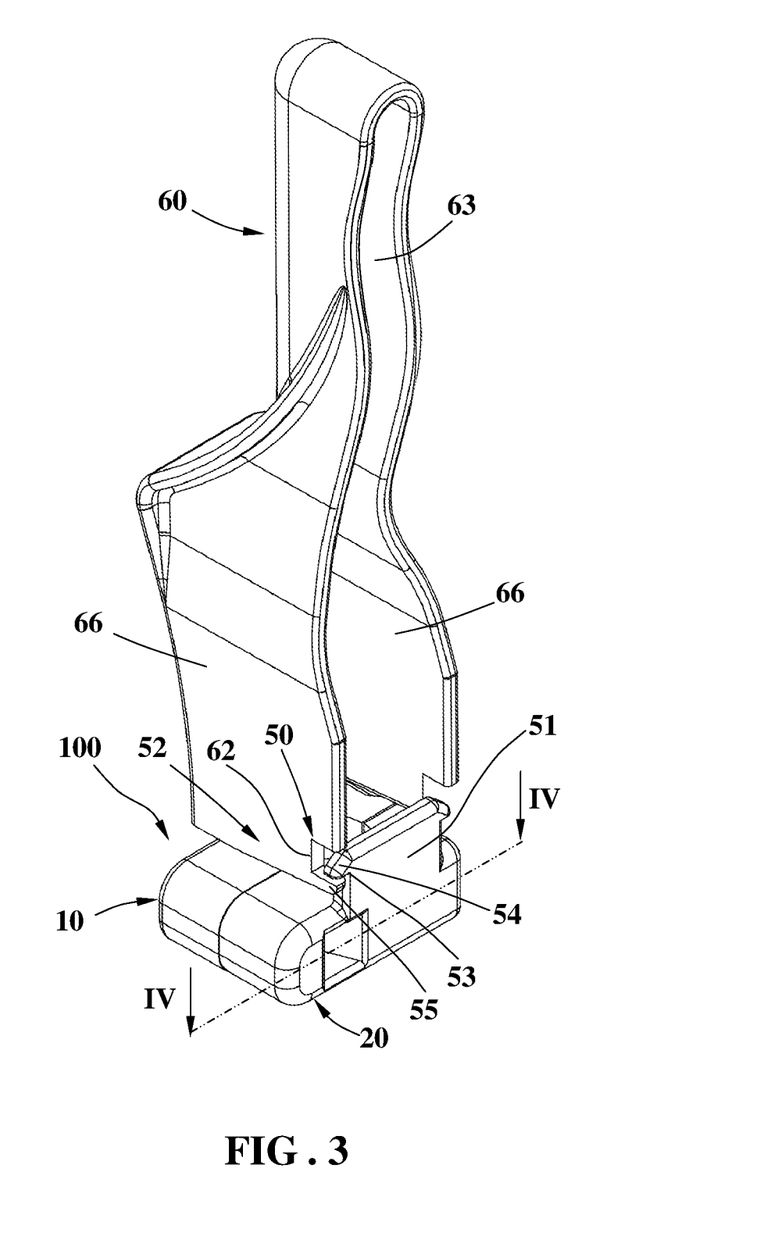
FIG. 3 is a perspective view of the syringe needle shield of the present invention.
Figure 4:
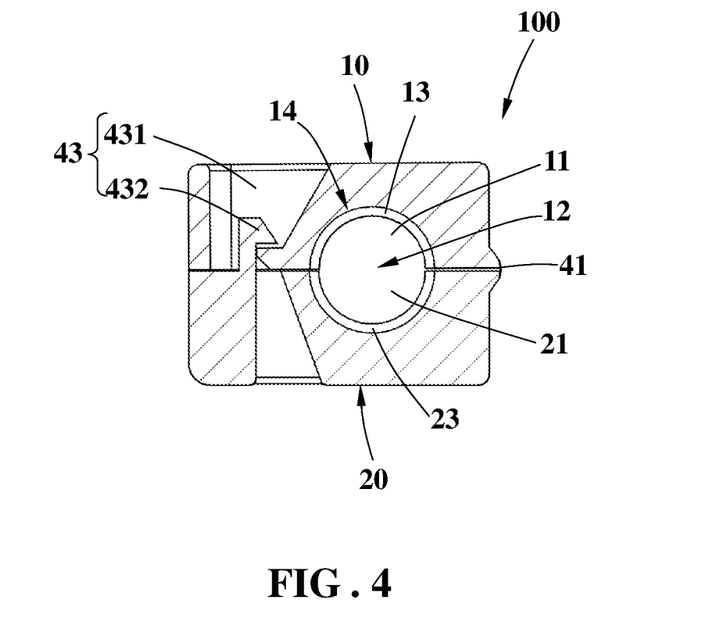
FIG. 4 is a cross sectional view, taken along plane IV-IV of FIG. 3.

As shown in FIGS. 2, 3 and 5, when the shield 60 is located at the second position P2, the restriction portion 53 is engaged with the engaging portion 55, and cannot be separated from the engaging portion 55 from the opposite direction. As shown in FIGS. 1-4, the first positioning portion 51 includes the restriction portion 53 protruding from two sides thereof, and each restriction portion 53 includes an inclined face 54 on the top thereof. The two sides of the shield 60 each have the engaging portion 55 that, when the shield 60 is moved from the first position P1 to the second position P2, is guided along the inclined face 54 to move under the restriction portion 53. Specifically, as shown in FIGS. 1-3, the two sides of the shield 60 respectively extend toward the first positioning portion 51. Each of the two sides of the shield 60 includes a notch 62 located corresponding to the restriction portion 53 on the same side. The engaging portion 55 is located at the lower portion of the notch 62. When the shield 60 moves from the first position P1 to the second position P2, the engaging portions 55 move along the inclined faces 54, and the engaging portions 55 are slightly deformed due to the flexibility of the plastic material, the engaging portions 55 slightly expand outward after passing the inclined faces 54 so as to pass the restriction portions 53. The engaging portions 55 eventually are located under the restriction portions 53. The notches 62 respectively accommodate the restriction portion 53 and the inclined face 54 corresponding thereto. The shield 60 cannot move back from the second position P2 to the first position P1, so that the used needle 73 will no longer be exposed by the shield 60.

As shown in FIGS. 6-9, the needle shield of the present invention further comprises a third part 30. The second side of the first part 10 is connected to the first side of the third part 30 by a pivotable second connection portion 42. A second snapping portion 44 includes an assistance hook 442 located at the inside of the third part 30, and an assistance recess 441 that is located at the outside of the second part 20. When the first part 10 is connected to the second part 20 by the first snapping portion 43, the third part 30 is pivotable toward the first part 10 and the second part 20 at the second connection portion 42, the assistance hook 442 is engaged with the assistance recess 441. The third part 30 is securely connected to the second snapping portion 44, so that the first and second parts 10, 20 cannot be separated from each other.

The restriction portions 53 and the engaging portions 55 may have different embodiments.

Figure 10:
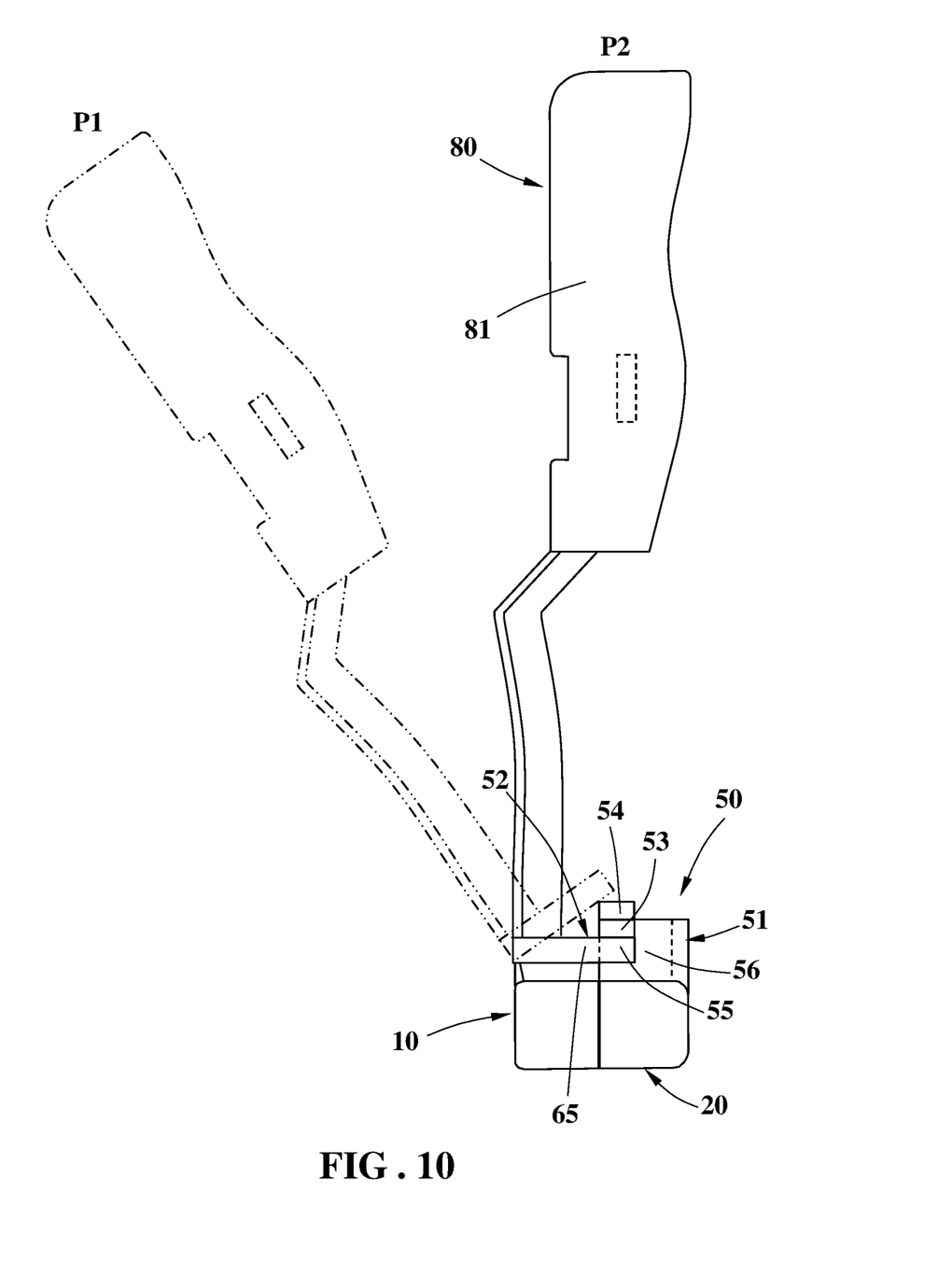
FIG. 10 is a left side view of the third embodiment of the present invention, and also shows that the shield is located at the first and second positions.
Figure 11:
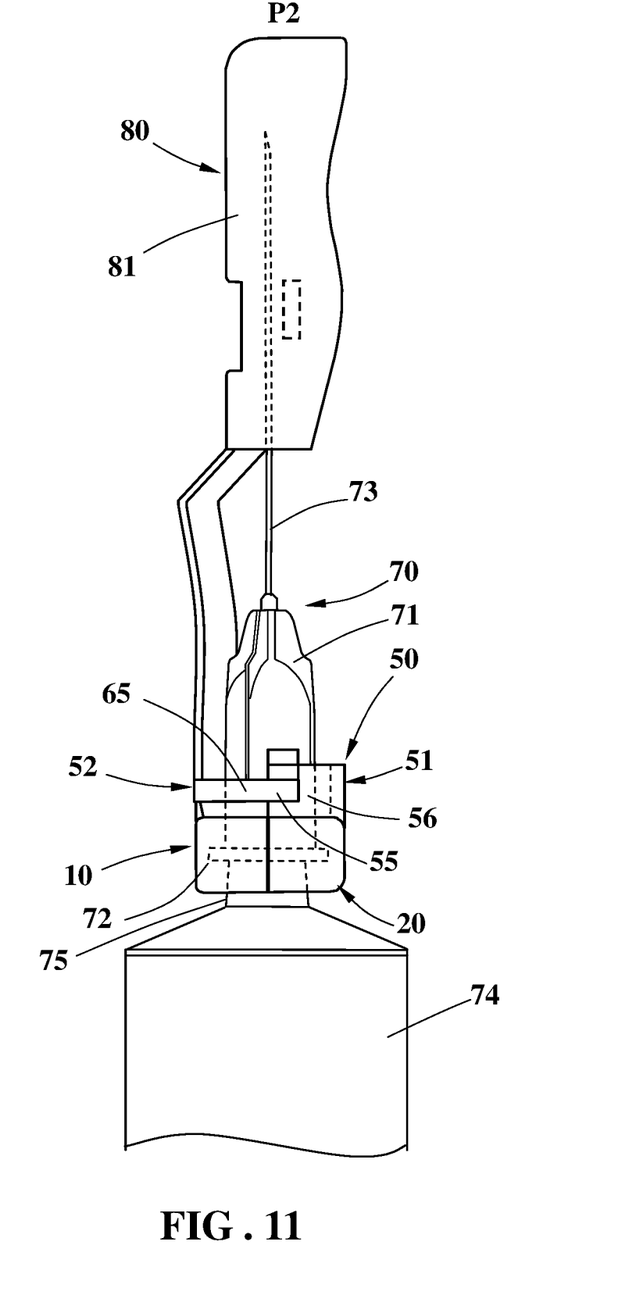
FIG. 11 is a left side view of the third embodiment of the present invention, and the syringe needle is shielded by the needle shield of the present invention.

As shown in FIGS. 1, 10 and 11, the two sides of the first positioning portion 51 respectively extend toward the shield 80 of another embodiment of the present invention. The restriction portion 53 and the inclined face 54 are located at an extension portion 56 of the first positioning portion 51. The two sides of the shield 80 extend toward the first positioning portion 51. The engaging portion 55 is located at an extension portion 65 of the shield 80. The way of engagement between the restriction 53 and the engaging portion 55 is the same as that disclosed in the previous embodiment.

Figure 12:
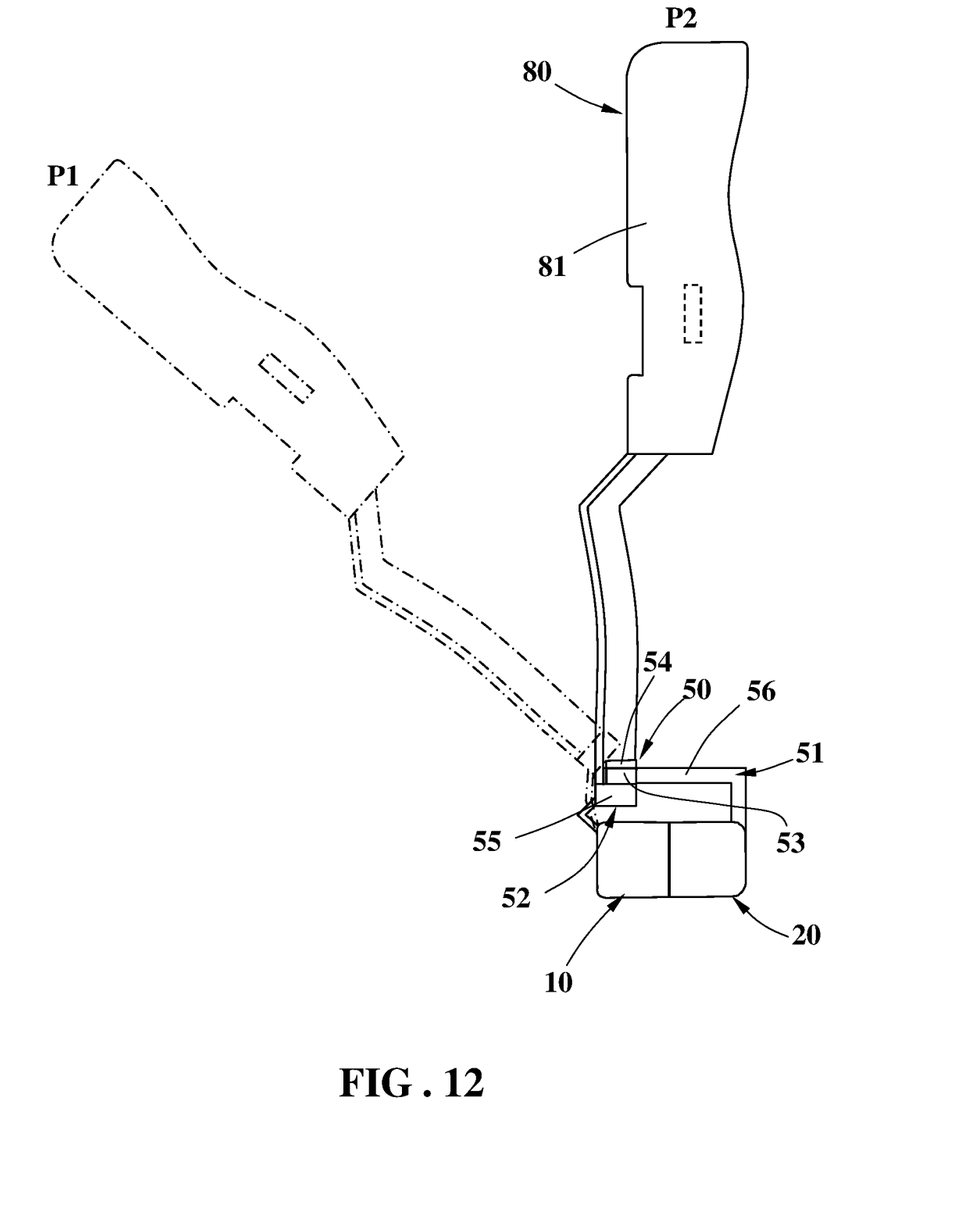
FIG. 12 is a left side view of the fourth embodiment of the present invention, and also shows that the shield is located at the first and second positions.
Figure 13:
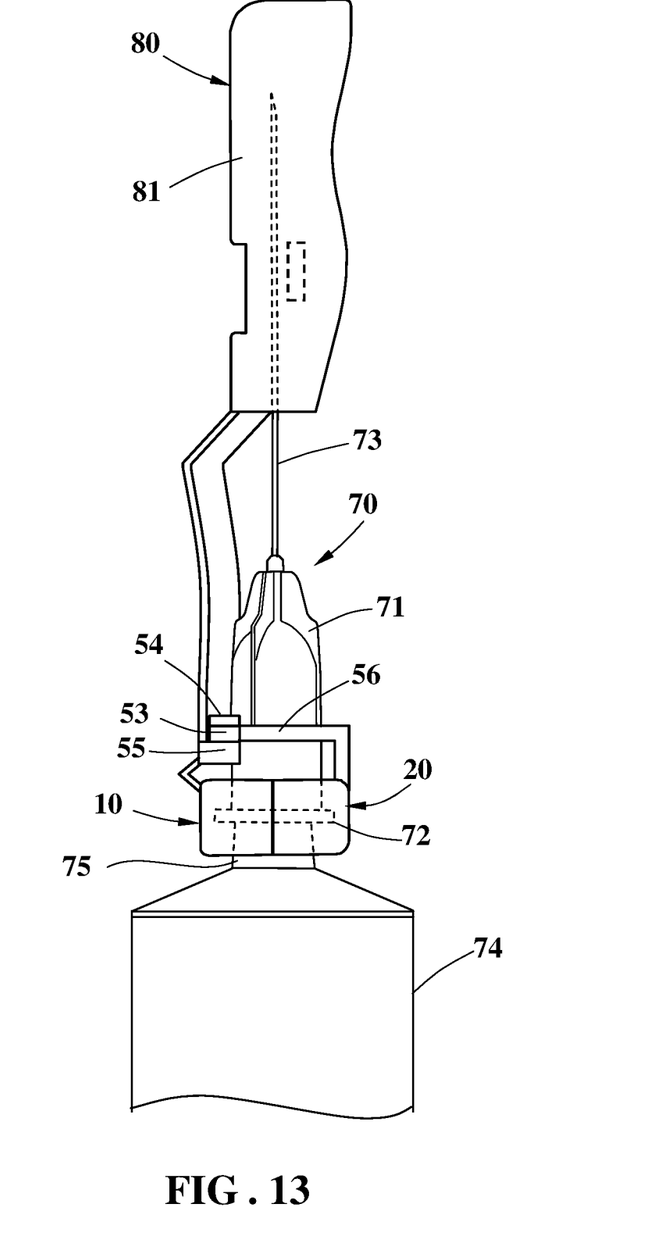
FIG. 13 is a left side view of the fourth embodiment of the present invention, and the syringe needle is shielded by the needle shield of the present invention.

As shown in FIGS. 12 and 13, the two sides of the first positioning portion 51 respectively extend toward the shield 80. The restriction portion 53 and the inclined face 54 are located at an extension portion 56 of the first positioning portion 51. The two sides of the lower end of the shield 80 do not extend toward the first positioning portion 51, and the engaging portions 55 are directly formed on the two sides of the lower end of the shield 80. The way of engagement between the restriction portions 53 and the engaging portions 55 is the same as that disclosed in the previous embodiment.

As shown in FIGS. 10-13, the shield 80 is different from the shield 60 in FIGS. 1-9, the shield 60 in FIGS. 1-9 has longer sidewalls 66, while the shield 80 in FIGS. 10-13 has shorter sidewalls 81.

The restriction portions 53 and the inclined faces 54 in the embodiments mentioned above are located at the second part 20, and the restriction portions 55 are located at the shields 60, 80. It is noted that the restriction portions 53 and the inclined faces 54 can be located at the shields 60, 80, and the restriction portions 55 are located at the second part 20.

As shown in FIGS. 1-5, in the first embodiment, the base 100 is composed of the first and second parts 10, 20, in the second embodiment as shown in FIGS. 6-9, the base 200 is composed of the first, second and third parts 10, 20, 30. The two bases 100, 200 can be widely used with the straight needle hub, the indwelling needle hub, the connector between winged infusion set and infusion tube, and the insulin syringe. The shield 60 can be changed according practical needs. The shield 80 in FIGS. 10-13 can be used with the base 100 or the base 200 as described above.

While we have shown and described the embodiment in accordance with the present invention, it should be clear to those skilled in the art that further embodiments may be made without departing from the scope of the present invention.

What is claimed is:

1. A syringe needle shield comprising:
   a first part and a second part, a first side of the first part connected to a first side of the second part by a pivotable first connection portion, the second part being pivotally movable toward the first part on the first connection portion;
   a first snapping portion including a recess inside of the first part and a hook inside of the second part, the hook being fixedly connected with the recess and cannot be separated from the recess when the second part is pivotally moved toward the first part;

a first room and a second room respectively defined in the first part and the second part, wherein when the first part is connected to the second part by the first snapping portion, the first room and the second room together define a chamber, the chamber being vertically defined through a top and a bottom of each of the first part and the second part, the chamber adapted to accommodate and restrict a needle hub of a syringe;

a first groove and a second groove respectively defined inside of the first part and the inside of the second part, and in communication with the first room and the second room, wherein when the first part is connected to the second part by the first snapping portion, the first groove and the second groove together define an annular groove inside of the chamber, the annular groove adapted to accommodate and restrict a flange of the needle hub;

a flexible plate connected between an underside of a shield and the first part, the shield pivotally movable from a first position to a second position; and a positioning device having a first positioning portion and a second positioning portion, the first positioning portion located at the second part, and the second positioning portion connected to the shield, the first positioning portion and the second positioning portion respectively including a restriction portion and an engaging portion, such that when the shield is located at the second position, the restriction portion is engaged with the engaging portion.

2. The syringe needle shield as claimed in claim 1, further comprising:

a third part, a second side of the first part connected to a first side of the third part by a pivotable second connection portion; and a second snapping portion including an assistance hook located inside of the third part and an assistance recess located outside of the second part, wherein when the first part is connected to the second part by the first snapping portion, the third part is pivotable toward the first part and the second part on the second connection portion, and the assistance hook is engaged with the assistance recess.

3. The syringe needle shield as claimed in claim 1, wherein the restriction portion extends from each of two sides of the first positioning portion, the restriction portion has an inclined face, each of two sides of the shield includes the engaging portion, and when the shield is moved from the first position to the second position the engaging portion is guided along the inclined face and enters into engagement with the restriction portion.

4. The syringe needle shield as claimed in claim 3, wherein the two sides of the shield respectively extend toward the first positioning portion, each of the two sides of the shield includes a notch located corresponding to the restriction portion corresponding thereto, the engaging portion is located at a lower portion of the notch which accommodates the restriction portion and the inclined face.

5. The syringe needle shield as claimed in claim 3, wherein the two sides of the first positioning portion respectively extend toward the shield, the two sides of the shield respectively extend toward the first positioning portion, the restriction portion and the inclined face are located at an extension portion of the first positioning portion, and the engaging portion is located at an extension portion of the shield.

6. The syringe needle shield as claimed in claim 3, wherein the two sides of the first positioning portion respectively extend toward the shield, and the restriction portion and the inclined face are located at an extension portion of the first positioning portion.

7. A base of a syringe needle shield comprising:

a first part and a second part, a first side of the first part connected to a first side of the second part by a pivotable first connection portion, the second part being pivotally movable toward the first part on the first connection portion;

a flexible plate connected between an underside of the shield and the first part;

a first snapping portion including a recess inside of the first part and a hook inside of the second part, the hook being fixedly connected with the recess and cannot be separated from the recess when the second part is pivotally moved toward the first part;

a first room and a second room respectively defined in the first part and the second part, wherein when the first part is connected to the second part by the first snapping portion, the first room and the second room together define a chamber, the chamber being vertically defined through a top and a bottom of each of the first part and the second part;

a first groove and a second groove respectively defined in the inside of the first part and the inside of the second part, and communicating with the first room and the second room, wherein when the first part is connected to the second part by the first snapping portion, the first groove and the second groove together define an annular groove inside of the chamber;

a third part, a second side of the first part connected to a first side of the third part by a pivotable second connection portion; and a second snapping portion including an assistance hook located inside of the third part and an assistance recess located outside of the second part, wherein when the first part is connected to the second part by the first snapping portion, the third part is pivotable toward the first part and the second part on the second connection portion, and the assistance hook is engaged with the assistance recess.

* * * * *